(12) United States Patent
Auda et al.

(10) Patent No.: US 6,586,366 B1
(45) Date of Patent: *Jul. 1, 2003

(54) HOMOGENOUS AGROCHEMICAL CONCENTRATES AND AGROCHEMICAL FORMULATIONS OBTAINED THEREFROM

(75) Inventors: Mahroussa Auda, Ghent (BE); Dirk Hoorne, Mechelen (BE); Lodewijk Maria Rogiers, Haacht (BE)

(73) Assignee: Imperial Chemical Industries Plc, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/586,666

(22) PCT Filed: Jul. 27, 1994

(86) PCT No.: PCT/GB94/01612
§ 371 (c)(1),
(2), (4) Date: May 17, 1996

(87) PCT Pub. No.: WO95/03881
PCT Pub. Date: Feb. 9, 1995

(30) Foreign Application Priority Data

Jul. 27, 1993 (GB) ............................................. 9315501

(51) Int. Cl.$^7$ ............................ A01N 25/00; C11D 3/22

(52) U.S. Cl. ..................... 504/116; 510/470; 510/242; 510/245; 510/251; 510/401; 510/417; 510/421; 510/432

(58) Field of Search ................................ 510/470, 242, 510/245, 251, 401, 417, 421, 432; 504/116

(56) References Cited

U.S. PATENT DOCUMENTS

| | | | | |
|---|---|---|---|---|
| 3,413,109 A | | 11/1968 | Vartiak | 71/65 |
| 3,833,502 A | | 9/1974 | Leary et al. | 252/49.5 |
| 4,315,765 A | | 2/1982 | Large | 71/87 |
| 4,364,930 A | * | 12/1982 | Griat et al. | 424/81 |
| 5,011,681 A | * | 4/1991 | Ciotti et al. | 424/81 |
| 5,047,079 A | * | 9/1991 | Djafar et al. | 71/86 |
| 5,133,897 A | * | 7/1992 | Balzer | 252/312 |
| 5,468,718 A | * | 11/1995 | Burval et al. | 504/206 |
| 5,494,938 A | * | 2/1996 | Kawa et al. | 514/786 |
| 5,605,651 A | * | 2/1997 | Balzer | 252/312 |
| 5,639,711 A | * | 6/1997 | Kassebaum et al. | 504/206 |

FOREIGN PATENT DOCUMENTS

| | | |
|---|---|---|
| DE | A 39 25 846 | 2/1991 |
| EP | A 0 299 654 | 1/1989 |
| EP | A 0 498 785 | 8/1992 |
| EP | A 0 507 047 | 10/1992 |
| WO | WO A 88 10069 | 12/1988 |
| WO | WO A 92 01508 | 2/1992 |

* cited by examiner

*Primary Examiner*—Charles Boyer
(74) *Attorney, Agent, or Firm*—Pillsbury Winthrop LLP

(57) ABSTRACT

Oil based emulsifiable concentrates include (a) at least one oil component; (b) at least one surfactant hydrocarboxyl saccharide, particularly a surfactant hydrocarbyl polysaccharide (HPS); and (c) at least one other non-ionic surfactant. The concentrates are typically homogeneous for at least 24 hours and emulsify readily on dilution into water. The concentrates preferably also include: (d) an antifoaming agent, especially a polysiloxane; and/or (e) at least one chemical agent specific to the intended use of the composition, such as an agrochemical, especially a herbicide, or a metal corrosion inhibitor. The concentrates can be diluted readily in water to give emulsion formulations which can be sprayed onto substrates, e.g. when the chemical agent is a herbicide, onto weeds.

21 Claims, No Drawings

HOMOGENOUS AGROCHEMICAL CONCENTRATES AND AGROCHEMICAL FORMULATIONS OBTAINED THEREFROM

This invention relates to surfactant compositions and in particular to compositions which contains a plurality of surfactants and at least one oil, and which is readily emulsifiable into water.

The invention provides a concentrate composition which comprises:
a at least one oil component;
b at least one surfactant hydrocarbyl saccharide, particularly a hydrocarbyl polysaccharide (HPS); and
c at least one other non-ionic surfactant.

The composition of the invention typically takes the form of an oil based concentrate which is homogeneous for at least 24 hours and which emulsifies readily on dilution into water.

The composition preferably also comprises
d an antifoaming agent; and/or
e at least one chemical agent specific to the intended use of the composition.

The composition including these further components is also typically homogeneous for at least 24 hours and emulsifies readily on dilution into water.

The chemical agent specific to the intended use of the composition may be, for example, an agrochemical or a metal corrosion inhibitor. The composition may however be used without any such specific chemical agent as a metal degreasing agent, or as a precursor for dilution with water for metal cutting fluids.

The concentrate composition may also comprise a water miscible liquid, which may be desirable if the viscosity of the composition would otherwise be inconveniently high. Such liquid may include or be water. The water content is preferably low enough for the composition to remain homogeneous for at least 24 hours after making up. The components and their proportions are preferably chosen such that where any components are readily available only as aqueous solutions (such as the HPS) the composition provided by mixing the composition components is stable, notwithstanding the water which is thereby introduced. When the concentrate composition includes water, the concentrate will usually be a solution of the water in the oil, the surfactant combination acting to solublise the water, or as a water-in-oil colloidal emulsion or a microemulsion in which the water is dispersed as very fine droplets such that the composition is clear or transparent.

The oil component typically has a boiling point of over 200° C. at atmospheric pressure and a melting point not higher than 60° C. It may comprise for example a mineral oil, an optionally hydrogenated vegetable oil, such as an optionally hydrogenated cotton seed oil, linseed oil, mustard oil, neem oil, niger seed oil, oiticica oil, olive oil, palm oil, palm kernel oil, peanut oil, perilla oil, poppy seed oil, rape seed oil, safflower oil, sesame oil, or soybean oil. An ester (especially a $C_1$ to $C_6$ ester) of a $C_8$ to $C_{22}$ fatty acid, especially a $C_{12}$ to $C_{18}$ fatty acid, e.g. methyl, ethyl or propyl laurate, heptadecanoate, heptadecenoate, heptadecadienoate, stearate or oleate, or a mixture thereof, e.g. an ester in which the total number of carbon atoms in the molecule does not exceed 20, and preferably an ester of a $C_{12}$ to $C_{15}$ fatty acid, e.g. methyl, ethyl or propyl laurate, or a mixture thereof.

The oil component preferably also contains or is associated with at least one oil soluble surfactant, especially such as can render the oil self emulsifiable into water. Such a surfactant may include at least one of relatively high HLB (hydrophilic lipophilic balance) in combination with one of low HLB, for example calcium stearate. Such an oil solution component may be in the form of a commercially available so-called "crop oil" or "oil adjuvant". A typical oil component contains 98 to 60, preferably 95 to 83, parts by weight of oil, and 2 to 40, preferably 5 to 17, parts by weight of oil soluble surfactant(s). When water is present in solublised form or as a colloidal emulsion or a microemulsion the oil soluble surfactant may be partitioned between oil phase and aqueous phases (or be present at the interface).

The surfactant hydrocarbyl saccharide may be a monoglycoside or a polyglycoside or mixture thereof. It is conventional to refer to hydrocarbyl saccharide surfactants as hydrocarbyl polysaccharides even where the saccharide moiety only contains one saccharide unit. Typically such surfactants are mixtures of compounds with monosaccharide and polysaccharide (including disaccharide) units. Among glycosides, compounds of particular use in this invention include compounds and mixtures of compounds of the formula:

$$ROG_a$$

where
R is a hydrophobic moiety;
G is a saccharide residue; and
a has an average value of at least 1.

The group R may be an optionally substituted hydrocarbyl group. In particular R can be an alkyl, cycloalkyl, aryl, alkaryl, aralkyl or alkenyl group and is preferably an alkyl group. The group R suitably contains from 4 to 30 carbon atoms, preferably up to 24 carbon atoms, more preferably from 6 to 18 carbon atoms and especially from 8 to 14 carbon atoms. Thus, R can be a mixture of alkyl or alkoxy groups which contain, on average, for example 8 to 14 carbon atoms.

The saccharide residue G may be derived from one or more of fructose, glucose, mannose, galactose, telose, gulose, allose, altrose, idose, arabinose, xylose, lyxose and ribose or from mixtures thereof. The group G is conveniently derived from glucose units and the glycoside is then a glucoside. If derived from sucrose the groups will comprise fructose and glucose residues.

The value of a is the degree of polymerisation. It typically has an average value of at least 1.1, preferably at least 1.2 and especially at least 1.3. The value of a is typically not greater than 8, and preferably not greater than 4, for example not greater than 2. When the glycoside is an alkyl glucoside, the value of a is conveniently between 1 and 2.

We have obtained useful results when the glycoside is an alkyl polyglucoside of the general formula:

$$C_nH_{(2n+1)}.O.(C_6H_{10}O_5)_b.H$$

where
n is from 8 to 14, and
b is greater than one and not more than two.

In particular, the glucoside may be one in which the average value of n is from 9 to 13 and especially about 10. The value of b is typically at least 1.3 and not more than 1.9. A particularly useful material of this type is one in which n is from 8 to 11 and has an average value of 10 and b is about 1.35. Surfactant hydrocarbyl saccharides are commercially available and the materials designated for example as APG 225 and APG 300 by Henkel or as sold under the trade name Triton BG 10 by Rohm & Haas can be used satisfactorily.

The other non-ionic surfactant(s) may be any which will give a composition which is stable and homogeneous for at least 24 hours after making up.

Preferred non-ionic surfactants are of the formula:

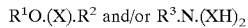

where
- $R^1$ is an alkyl or alkenyl group, which suitably contains up to 24, preferably 6 to 21, and especially 9 to 18, carbon atoms, e.g. lauryl, heptadecyl, heptadeceyl, heptadecadienyl, stearyl or oleyl, an alkyl phenyl group having 6 to 12 carbon atoms in its alkyl group, a sorbitan group or a group of formula $R^4CO$, where $R^4$ is an alkyl group having 11 to 22 carbon atoms;
- $R^2$ is hydrogen or an alkyl group, a carboxyalkyl group, for example carboxyalkyl having 2 to 4 carbon atoms, such as carboxy-methyl, -ethyl or -propyl, or a salt thereof, or a fatty acid residue having 10 to 22 carbon atoms, e.g. laurate, heptadecanoate, heptadecenoate, heptadecadienoate, stearate or oleate;
- X is a polyalkylene oxide group containing an average of 2 to 40, preferably from 2 to 13, and especially from 2 to 10, alkylene oxide groups or mixed alkylene oxide groups, where the alkylene groups each have 2 to 8, preferably 2 or 3, carbon atoms;
- $R^3$ is an alkyl or alkenyl group having 10 to 22 carbon atoms.

The relative proportions of the oil component (a), the surfactant hydrocarbyl saccharides (b) and the other non-ionic surfactant (c) are suitably (by weight):
- a 40 to 70, especially 55 to 63,
- b 5 to 30, especially 5 to 25, and
- c 10 to 40, especially 15 to 30.

If an antifoaming agent is present, it should be in a quantity sufficient to secure an adequate anti-foaming effect for the intended use of the composition without separating from the composition, normally 0.05 to 10% and preferably 0.2 to 6% by weight of the total position.

The antifoaming agent(s) is preferably one or more polysiloxanes, especially of the type having hydrophilic groups. It is preferably of formula:

where
- each $R^5$ is independently an alkyl group, preferably having 1 to 3 carbons atoms and are desirably methyl groups;
- one or more of the groups $R^6$ may be residues of polyalkylene glycols and the others are as defined for $R^5$ (desirably all the groups $R^6$ are as defined for $R^5$ and are particularly methyl groups).

Typically the molecular weight of the polysiloxane antifoam will be in the he range 1000 to 20000 especially 5000 to 15000. Examples of suitable polysiloxane antifoams are disclosed in British Patents 1533610 and 1554736.

Any chemical agent specific to the intended use of the composition may be for example an agrochemical or a metal corrosion inhibitor.

If an agrochemical is present it is typically one or more growth regulators, herbicides, and/or pesticides, for example insecticides, fungicides or acaricides.

The composition according to the invention may however be used without any specific chemical agent as a metal degreasing agent, or as a precursor for dilution with water for metal cutting fluids.

The invention includes a process for making the composition of the invention which comprises mixing the components together.

The invention further includes a diluted formulation which comprises a composition comprising components (a), (b) and (c) according to the invention with from 10 to 10,000 times the weight of the composition of water. The concentrate compositions of the invention emulsify readily on dilution in water to form the formulation. At relatively low levels of dilution, the product will be an oil-in-water emulsion having a relatively high concentration of oil. This intermediate emulsion can subsequently be further diluted by water or an aqueous solution or suspension of other components desired in the final formulation.

The diluted formulations can be made up in various ways. Thus, where the formulation does not comprise components other than (a), (b), (c) and water, the formulation can be made up by simply mixing the composition of components (a), (b) and (c) with water.

Where the formulation comprises the composition of components (a), (b) and (c) and a chemical agent (d), for example an agrochemical or a metal corrosion inhibitor, and/or an antifoaming agent (e), to secure an adequate anti-foaming effect for the intended use of the formulation, the formulation may be made up for example by:
- i mixing the components (a), (b), (c) and (d) and/or (e) to form an oil based emulsifiable concentrate composition of the invention and then diluting the composition by mixing it with water to form the formulation,
- ii mixing components (a), (b) and (c) to form a an oil based emulsifiable concentrate composition of the invention and diluting the composition with water to form a first formulation component, as appropriate mixing the components (d) and/or (e) and diluting the mixture of these components with water, and mixing the first formulation component and the mixture to form the desired formulation, or
- iii mixing components (a), (b) and (c) and optionally one of components (d) and/or (e) to form an oil based emulsifiable concentrate composition of the invention, separately mixing with or dissolving in water one or both of components (d) and/or (e) and mixing the concentrate composition into this mixture or solution.

In all such methods for making a formulation according to the invention, the ratio of the weight of water used to the total weight of the components (a), (b) and (c) will typically be adjusted as appropriate to give a final formulation of the components (a), (b) and (c) within the definition above.

In a still further aspect, the invention provides a method of applying a formulation of the invention to a substrate. Embodiments of this method include:
- i a method of treating vegetation by applying to plants and/or soil such a formulation according to the invention which formulation comprises a specific chemical agent which is an agrochemical.
- ii a method of working metal which comprises applying a formulation according to the invention to the metal which formulation optionally comprises a specific chemical agent which is a metal corrosion inhibitor.

In embodiment (i) the agrochemical may be one or more growth regulators, herbicides, and/or pesticides, for example insecticides, fungicides or acaricides. This embodiment of the invention of the method of applying the formulation accordingly includes: a method of killing or inhibiting vegetation by applying the formulation which comprises a specific chemical agent which is one or more growth regulators and/or herbicides, and a method of killing or inhibiting plant pests by applying the formulation which comprises a specific chemical agent which is one or more pesticides, for example insecticides, fungicides or acaricides. In embodiment (i), the effect of the agrochemical, whether one or more growth regulators, herbicides, and/or pesticides, for example insecticides, fungicides or acaricides, may be potentiated by the oil component and/or the HPS.

In embodiment (ii) the working of the metal may include for example cutting or abrasion.

Within compositions and formulations of the present invention which comprise as component (d) an agrochemical which is typically one or more growth regulators, herbicides, and/or pesticides, for example insecticides, fungicides or acaricides, examples of such agrochemicals which growth regulators, herbicides, etc. include phosphonomethyl-n-carboxyethyl (PMCM) compounds and related compounds of the formula:

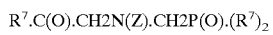

R$^7$.C(O).CH2N(Z).CH2P(O).(R$^7$)$_2$ where each R$^7$ is independently halogen, —NHOH, —N(R$^8$)$_2$, —OR$^9$, —SR$^9$ or —OM, where R$^8$ is independently a hydrogen, or alkyl or hydroxyalkyl, preferably containing less than about 5 carbon atoms, alkenyl, preferably containing less than about 5 carbon atoms, or phenyl;

each R$^9$ is independently hydrogen, alkyl, hydroxyalkyl or chloroalkyl, preferably containing less than about 5 carbon atoms, alkoxy, preferably containing less than about 5 carbon atoms, alkylene amine, preferably containing less than about 12 carbon atoms, phenyl or benzyl;

M is hydrogen or an agriculturally acceptable salt forming moieties such as alkali metal, alkaline earth metal, stannic, ammonium, organic ammonium, alkyl sulfonium, alkyl sulfoxonium, alkyl phosphonium moieties or combinations thereof; and Z is hydrogen, an organic moiety or an inorganic moiety.

Representative patents disclosing at least some of such compounds include U.S. Pat. Nos. 3,799,758, 4,397,676, 4,140,513, 4,315,765, 3,868,407, 4,405,531, 4,481,026, 4,414,158, 4,120,689, 4,472,189, 4,341,549 and 3,948,975. Patents disclosing PMCM compounds wherein Z is other than hydrogen include U.S. Pat. Nos. 3,888,915, 3,933,946, 4,062,699, 4,119,430, 4,322,239 and 4,084,954.

In preferred PMCM compounds,

Z is hydrogen or an organic substituent;

R$^9$ is independently selected from hydrogen, alkyl, hydroxyalkyl or chloroalkyl, preferably containing less than about 5 carbon atoms, alkoxy, preferably containing less than about 5 carbon atoms, alkylene amine, preferably containing less than about 12 carbon atoms, phenyl or benzyl moieties; and M is selected from hydrogen and agriculturally acceptable salt forming moieties alkali metal, phosphonium moieties or combinations thereof.

Representative patents disclosing at least some of such compounds include U.S. Pat. Nos. 3,799,758, 4,397,676, 4,140,513, 4,315,765, 3,868,407, 4,405,531, 4,481,026, 4,414,158, 4,120,689, 4,472,189, 4,341,549 and 3,948,975. Patents disclosing PMCM compounds wherein Z is other than hydrogen include U.S. Pat. Nos. 3,888,915, 3,933,946, 4,062,699, 4,119,430, 4,322,239 and 4,084,954.

In preferred PMCM compounds, Z is hydrogen or an organic substituent such as methylene carboxylic; methylene phosphonic; and methylene cyano. Other organic substituents include carboxyl, such as formyl, acetyl, benzoyl, perfluoroacyl and thiocarbonyl; ethylene, such as cyano, carbamoyl or carboxy substituted ethyl; and benzene sulphonyl substituents. Patents disclosing compounds where the nitrogen has three organic substituents include U.S. Pat. Nos. 3,455,675, 3,556,762, 3,853,530, 3,970,695, 3,988,142, 3,991,095, 3,996,040, 4,047,927, 4,180,394, 4,203,756, 4,261,727 and 4,312,662. A preferred tertiary nitrogen substituted PMCM compound is N,N-bis(phosphonomethyl) glycine.

Those PMCM compounds where Z is hydrogen are most preferred when the phytoactivity desired is herbicidal activity.

The above listed patents are incorporated herein by reference.

Illustrative examples of agriculturally acceptable salt forming moieties represented by M, as in OM, are the alkali metals having atomic weights of from 22 to 133, inclusive, such as sodium, potassium, or rubidium; the alkaline earth metals having atomic weights of from 24 through 88 inclusive, such as magnesium or calcium; ammonium and aliphatic ammonium, wherein the aliphatic is primary, secondary, tertiary or quaternary and preferably wherein the total number of carbon atoms does not exceed more than about twelve; phenylammonium; trialkylsulphonium, preferably wherein the total number of carbons in the three alkyl substituents does not exceed more than about six, such as trimethylsulphonium, ethyl dimethylsulphonium, propyl dimethylsulphonium and the like; trialkylsulphoxonium, preferably wherein the total number of carbon atoms in the three alkyl substituent does not exceed more than about six, such as trimethylsulphoxonium, ethyl dimethylsulphoxonium, propyl dimethylsulfoxonium and the like; tetraalkylphosphonium, such as tetramethylphosphonium, ethyl trimethylphosphonium, propyl trimethylphosphonium and similar groups.

In desirable compositions according to this invention, M is independently selected from the above described agriculturally acceptable salt forming moieties and hydrogen. In more desirable compositions, M is an alkali metal, ammonium, monoalkyl ammonium or trialkylsulphonium moiety. In especially desirable compositions only one M is an alkali metal, ammonium, monoalkyl ammonium, or trialkylsulphonium moiety, while the two M's are hydrogen. Particularly desirable compositions include isopropylamine N-phosphonomethylglycine, trimethylsulphonium N-phosphonomethylglycine and sodium sesqui-N-phosphonomethylglycine. Combinations of two or more PMCM compounds can be employed in the composition formulation and methods of the present invention.

The present invention is illustrated by the following Examples. All parts and percentages are by weight unless otherwise stated.

Materials

HPS hydrocarbyl polysaccharide of the formula ROG$_a$ where G is a glucose residue, a is on average 1.5, and R is a C$_9$ average alkyl group as a 75% by weight aqueous solution (75% HPS:25% water).

Oil Components:

| | |
|---|---|
| 01 | 83% Mineral Oil + 17% ATPLUS 300 surfactant (from ICI) |
| 02 | 83% methyl laurate + 17% ATLOX 5405 B surfactant (from ICI) |
| 03 | Mineral Oil |

Non-Ionic Surfactant Components:

| | |
|---|---|
| N1 | (ethylene oxide)$_4$ lauryl alcohol |
| N2 | (ethylene oxide)$_{10}$ oleyl alcohol |
| N3 | (ethylene oxide)$_5$ sorbitan monolaurate |
| N4 | (ethylene oxide)$_{2.5}$ C$_{12}$ to C$_{15}$ alcohol methylcarboxylate |
| N5 | (ethylene oxide)$_6$-(propylene oxide)$_3$ C$_{12}$ to C$_{15}$ alcohol |
| AF | Antifoam - Polysiloxane SURFYNOL DF58 |

EXAMPLE 1

Oil based emulsifiable concentrate Compositions 1 to 10 were made up by mixing together with stirring the components listed below in the amounts given in Table 1 below. Each of Compositions 1 to 10 was a homogeneous stable solution which readily emulsified when diluted in to water.

EXAMPLE 2

Formulations 1 to 4 were made by preparing four solutions of herbicide, made by dissolving the selective herbicide trimethyl-sulphonium N-phosphonomethylglycine (2 1, 72% w/w aqueous water) in water (300 1), and into each solution 250 or 750 ml of one of Compositions 5 and 10 were emulsified. This gave dilution rates for Formulations 1 and 3 of 0.08% and 2 and 4 of 0.252.

EXAMPLE 3

Formulations 1 and 2 were sprayed at the rates shown in Table 2 onto *Cirsium arvense* (CIRAR) and *Amaranthus retroflexus* (AMARE) using van der We spray equipment fitted with Teejet 11003 nozzles at 3 bar pressure. Visual evaluation of the weed control was performed 7, 14 and 28 days after treatment and the percentage of dead plants compared with an untreated control was assessed as the % control. The spray tests were carried out in four replicates and the results expressed as the mean of the four replicates. The formulations and test results are set out in Table 2 below.

TABLE 1

| Comp No | Components (% w/w) | | | | | | | | | |
|---|---|---|---|---|---|---|---|---|---|---|
| | HPS | 01 | 02 | 03 | N1 | N2 | N3 | N4 | N5 | AF |
| 1 | 20 | 60 | | | 20 | | | | | |
| 2 | 20 | | 60 | | 20 | | | | | |
| 3 | 20 | 60 | | | | 20 | | | | |
| 4 | 20 | 60 | | | | | 20 | | | |
| 5 | 20 | 60 | | | | | | 20 | | |
| 6 | 30 | | | 40 | | | 30 | | | |
| 7 | 20 | 59.8 | | | | | 20 | | 0.1 | 0.1 |
| 8 | 20 | 59.8 | | | | 20 | | | 0.1 | 0.1 |
| 9 | 20 | 59.8 | | | | | | 20 | 0.1 | 0.1 |
| 10 | 20 | | 60 | | | 20 | | | | |

TABLE 2

| Comp No | Form No | Rate (1/ha) | Days | % Control | |
|---|---|---|---|---|---|
| | | | | CIRAR | AMARE |
| 5 | 1 | 2 | 7 | 0 | 0 |
| | | | 14 | 41.5 | 82.0 |
| | | | 28 | 43.2 | 84.0 |
| | 2 | | 7 | 0 | 0 |
| | | | 14 | 47.0 | 85.0 |
| | | | | 49.5 | 94.0 |
| 10 | 3 | 2 | 7 | 0 | 0 |
| | | | 14 | 46.7 | 84.0 |
| | | | 28 | 50.5 | 89.7 |
| | 4 | | 7 | 0 | 0 |
| | | | 14 | 60.2 | 89.7 |
| | | | 28 | 65.5 | 95.2 |

What is claimed is:

1. A homogeneous agrochemical oil based composition for agrochemical use comprising:
   a. from 40 to 70 parts by weight of at least one oil component;
   b. from 5 to 30 parts by weight of at least one surfactant hydrocarbyl saccharide; and
   c. from 10 to 40 parts by weight of at least one other non-ionic surfactant; the concentrate emulsifying readily on dilution into water.

2. A homogeneous agrochemical composition according to claim 1, additionally comprising
   d. antifoaming agent.

3. A homogeneous agrochemical composition according to claim 2, wherein the antifoaming agent is present in amount of 0.05 to 10% by weight of the total composition.

4. A homogeneous agrochemical composition according to claim 1, in which the relative proportions of components (a), (b) and (c) are as follows:
   a. 55 to 63,
   b. 5 to 25, and
   c. 15 to 30.

5. A homogeneous agrochemical composition according to claim 1, wherein the oil component comprises mineral oil, vegetable oil, hydrogenated vegetable oil, ester oil, or mixture thereof.

6. A homogeneous agrochemical composition according to claim 5, further comprising
   e. oil soluble surfactant.

7. A homogeneous agrochemical composition according to claim 6, comprising 98 to 60 parts by weight of oil component and 2 to 40 parts by weight of oil soluble surfactant, based on the total weight of oil component and oil soluble surfactant.

8. A homogeneous agrochemical composition according to claim 1, wherein the surfactant hydrocarbyl saccharide is or includes at least one compound of formula:

$$ROG_a$$

wherein,
   R is a hydrophobic moiety;
   G is a saccharide residue; and
   a as an average value of at least 1.

9. A homogeneous agrochemical composition according to claim 8, wherein the surfactant hydrocarby saccharide is an alky polyglucoside of general formula:

$$C_nH_{2n+1}.O.(C_6H_{10}O_5)_b.H$$

where
   n is from 8 to 14, and
   b is greater than one and not more than two.

10. A homogeneous agrochemical composition according to claim 1, wherein the other non-ionic surfactant is of the formula:

$$R^1O.(X).R^2 \text{ and/or } R^3.N.(XH)_2$$

where
$R^1$ is an alkyl or alkenyl group containing up to 24 carbon atoms, an alkyl phenyl group having 6 to 12 carbon atoms in its alkyl group, a sorbitan group or a group of formula $R^4CO$ where $R^4$ is an alkyl group having 11 to 22 carbon atoms;
$R^2$ is hydrogen or an alkyl group, a carboxyalkyl group, or a salt thereof, or a fatty acid residue having 10 to 22 carbon atoms;
X is a polyalkylene oxide group containing an average of 2 to 40 alkylene oxide groups or mixed alkylene oxide groups, where the alkylene groups each have 2 to 8 carbon atoms;
$R^3$ is an alkyl or alkenyl group having 10 to 22 carbon atoms.

11. A homogeneous composition as claimed in claim 2, wherein the antifoaming agent is of the formula:

$$R^5_3.SiO.\{SiO.R^5.R^6\}_n.Si.R^5_3$$

where
each $R^5$ is independently an alkyl group;
one or more of the groups $R^6$ may be residues of polyalkylene glycols and the others are as defined for $R^5$.

12. A homogeneous agrochemical composition according to claim 1, wherein the composition contains as the agrochemical, one or more of growth regulators, herbicides and/or pesticides.

13. A diluted homogeneous agrochemical formulation comprising the composition according to claim 1 and from 10 to 10,000 times the weight of the composition of water.

14. A composition obtained by combining
(i) water;
(ii) an homogeneous:concentrate comprising:
  a. from 40 to 70 parts by weight of at least one oil component;
  b. from 5 to: 30 parts by weight of at least one surfactant hydrocarbyl saccharide; and
  c. from 10 to 40 parts by weight of at least one other non-ionic surfactant; with
(iii) an active agrochemical compound.

15. The composition according to claim 14, wherein the active agrochemical compound comprises growth regulator.

16. The composition according to claim 14, wherein the active agrochemical compound comprises herbicide.

17. The composition according to claim 14, wherein the active agrochemical compound comprises pesticide.

18. A homogeneous oil based concentrate composition for agrochemical use, which comprises:
a. from 40 to 70 parts by weight of at least one oil component;
b. from 5 to 30 parts by weight of at least on e surfactant hydrocarbyl saccharide;
c. from 10 to 40 parts by weight of at least one other non-ionic surfactant;
d. from 0 to 10% by weight of the total composition of an antifoaming agent, and
e. at least one agrochemical selected from growth regulators, herbicides, and/or pesticides;
the concentrate emulsifying readily on dilution into water.

19. The homogeneous composition according to claim 18, wherein the antifoaming agent is present in amount of 0.005 to 10% by weight of the total composition.

20. The homogenous composition according to claim 18, wherein the other non-ionic surfactant is of the formula:

$$R^1O.(X).R^2 \text{ and/or } R^3.N.(XH)_2$$

where
$R^1$ is an alkyl or alkenyl group containing up to 24 carbon atoms, an alkyl phenyl group having 6 to 12 carbon atoms in its alkyl group, a sorbitan group or a group of formula $R^4CO$ where $R^4$ is an alkyl group having 11 to 22 carbon atoms;
$R^2$ is hydrogen or an alkyl group, a carboxyalkyl group, or a salt thereof, or a fatty acid residue having 10 to 22 carbon atoms;
X is a polyalkylene oxide group containing an average of 2 to 40 alkylene oxide groups or mixed alkylene oxide groups, where the alkylene groups each have 2 to 8 carbon atoms;
$R^3$ is an alkyl or alkenyl group having 10 to 22 carbon atoms.

21. An agrochemical formulation obtained by diluting the composition of claim 18, with from 10 to 10,000 times the weight of the composition of water.

* * * * *